(12) United States Patent
Hungerford et al.

(10) Patent No.: US 8,172,798 B2
(45) Date of Patent: May 8, 2012

(54) SYSTEM AND METHOD FOR MANAGING INFUSION THERAPIES

(75) Inventors: Roger L. Hungerford, Medina, NY (US); Tuan Bui, Buffalo, NY (US); Gary Colister, Clarence, NY (US)

(73) Assignee: Sigma International General Medical Apparatus LLC, Medina, NY (US)

( * ) Notice: Subject to any disclaimer, the term of this patent is extended or adjusted under 35 U.S.C. 154(b) by 260 days.

(21) Appl. No.: 12/464,297

(22) Filed: May 12, 2009

(65) Prior Publication Data

US 2010/0292645 A1   Nov. 18, 2010

(51) Int. Cl.
*A61M 1/00* (2006.01)
(52) U.S. Cl. ........................................... 604/151
(58) Field of Classification Search ............... 604/65–67, 604/131, 890.1, 151; 128/DIG. 12, DIG. 13
See application file for complete search history.

(56) References Cited

U.S. PATENT DOCUMENTS

| | | | |
|---|---|---|---|
| 5,317,506 A | 5/1994 | Coutre et al. |
| 5,781,442 A | 7/1998 | Engleson et al. |
| 6,519,569 B1 | 2/2003 | White et al. |
| 6,671,563 B1 | 12/2003 | Engelson et al. |
| 6,731,989 B2 | 5/2004 | Engleson et al. |
| 6,847,899 B2 | 1/2005 | Allgeyer |
| 6,915,170 B2 | 7/2005 | Engleson et al. |
| 7,236,936 B2 | 6/2007 | White et al. |
| 2001/0049608 A1 | 12/2001 | Hochman |
| 2004/0176984 A1 | 9/2004 | White et al. |
| 2004/0193453 A1 | 9/2004 | Butterfield et al. |
| 2005/0102167 A1 | 5/2005 | Kapoor |
| 2007/0210157 A1 | 9/2007 | Miller |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2008/0071210 A1 | 3/2008 | Moubayed et al. |
| 2008/0154177 A1 | 6/2008 | Moubayed et al. |

FOREIGN PATENT DOCUMENTS

WO   2005010796   2/2005

OTHER PUBLICATIONS

WO 2005/010796, Mullan et al., publication date Mar. 2, 2005.*

* cited by examiner

*Primary Examiner* — Manuel Mendez
(74) *Attorney, Agent, or Firm* — Simpson & Simpson, PLLC

(57) ABSTRACT

A system for managing an infusion therapy, including: a server in communication with a central server; and an infusion pump in wireless communication with the server and for: uploading respective label data from respective labels for at least one medication, the respective label data including respective label pump programming data for infusion of the at least one medication by the pump; wirelessly transmitting the uploaded label data to the server; and wirelessly transmitting pump data identifying the pump to the server. The server is for transmitting the pump data and the respective label data to the server; and receiving, from the central server and in response to receipt of the pump data and the respective label data by the central server, second pump programming data regarding a second medication. The server is for comparing the first pump programming data with the second pump programming data.

12 Claims, 5 Drawing Sheets

SYSTEM AND METHOD FOR MANAGING INFUSION THERAPIES

FIELD OF THE INVENTION

The invention relates generally to a system and method for controlling an infusion pump having access to a central server. In particular the invention relates to a system and method including a server connected to the central server and in wireless communication with the pump.

BACKGROUND OF THE INVENTION

To control dispensing of medications, the prior art teaches systems or methods using a centralized server to acquire and compare patient, medication, and prescription information. The prior art also teaches systems or methods using a bed-side point of care device to perform comparisons regarding control of medications. For example, a scanner for a computer is used to scan patient, medication, and prescription information into the computer and the computer performs comparison functions.

SUMMARY OF THE INVENTION

The invention broadly comprises a system for managing an infusion therapy, including: a server in communication with a central server; and an infusion pump in wireless communication with the server and for: uploading respective label data from respective labels for at least one medication, the respective label data including respective label pump programming data for infusion of the at least one medication by the pump; wirelessly transmitting the uploaded label data to the server; and wirelessly transmitting pump data identifying the pump to the server. When the at least one medication consists of a single medication and the respective label pump programming data consists of first pump programming data, the server is for: transmitting the pump data to the central server; and receiving, from the central server and in response to receipt of the pump data by the central server, second pump programming data regarding a second medication. When the at least one medication includes a plurality of medications and the respective label pump programming data includes first pump programming data for a first medication from the plurality of medications, the server is for: transmitting the pump data to the central server; transmitting the respective label data to the server; and receiving, from the central server and in response to receipt of the pump data and the respective label data by the central server, second pump programming data regarding a second medication. The server is for comparing the first pump programming data with the second pump programming data.

In one embodiment, when the first pump programming data is the same as the second pump programming data, the server is for generating and wirelessly transmitting to the pump an authorization signal; or when the first pump programming data is the same as the second pump programming data, the server is for generating and wirelessly transmitting to the pump an authorization signal and the pump is for infusing the first medication only if the authorization signal is received in the pump.

In another embodiment, when the first pump programming data is different than the second pump programming data, the server is for generating and wirelessly transmitting to the pump a difference signal regarding the difference between the first and second pump programming data; or when the first pump programming data is different than the second pump programming data, the server is for generating and wirelessly transmitting to the pump a difference signal regarding the difference between the first and second pump programming data; and wirelessly transmitting to the pump the second pump programming data.

In one embodiment, the respective label programming data includes first medication data identifying the single medication or the first medication, and the second pump programming data includes second medication data identifying the second medication and the server is for comparing the first and second medication data and when the first and second medication data match, generating and wirelessly transmitting to the pump an authorization signal. In another embodiment, the respective label programming data includes first medication data identifying the single medication or the first medication, and the second pump programming data includes second medication data identifying the second medication, the server is for comparing the first and second medication data and when the first and second medication data match, generating and wirelessly transmitting to the pump an authorization signal. The pump is for infusing the first medication only if the authorization signal is received by the pump.

In one embodiment, the first programming data includes first medication data identifying the first medication and the second pump programming data includes second medication data identifying the second medication, the server is for comparing the first and second medication data and when the first and second medication data are different, generating and wirelessly transmitting to the pump a difference signal regarding the difference between the first and second medications.

In one embodiment, the respective label data includes label patient data identifying the patient for whom the at least one medication is prescribed and first medication identification data identifying the first medication, and the central server stores a list of patients including respective list patient identification data, respective list pump programming data, and respective prescribed medication identification data for patients in the list. The central server is arranged to: receive, from a bedside scanning device, the pump data and patient data identifying a patient in whom the pump is intended to infuse the at least one medication; and identify, using the patient data, first list patient identification data, first list pump programming data, and first prescribed medication identification data from the list of patients, the identification of the patient for the patient data and for the first list patient identification data being the same. Or, the server is arranged to: identify first list patient identification data, first list pump programming data, and first prescribed medication identification data from the list of patients by using the patient data and the first medication identification data. The identification of the patient for the patient data and for the first list patient identification data are the same and the respective medications identified by the first medication identification data and the first list prescribed medication identification data are the same. The central server is arranged to: correlate the first list patient identification data and the first list pump programming data with the pump data; or, correlate the first list patient identification data, the first list pump programming data, and the first prescribed medication identification data with the pump data. The central server is arranged to: select the first list pump programming data as the second pump programming data by using the correlation of the first list patient identification data, the first list pump programming data, or the first prescribed medication identification data with the pump data. The server is for receiving, from the central server, the first list patient identification data; and comparing the label patient identification data with the first list patient identification data.

In one embodiment, when the label patient identification data matches the first respective patient identification data, the server is for generating and wirelessly transmitting to the pump an authorization signal. In another embodiment, when the label patient identification data matches the first respective patient identification data, the server is for generating and wirelessly transmitting to the pump an authorization signal and the pump is for infusing the first medication only if the authorization signal is received by the pump. In a further embodiment, when the label patient identification data does not match the first respective patient identification data, the server is for generating and wirelessly transmitting to the pump a difference signal regarding the difference between the first patient identification data and the first respective patient identification data.

The invention also broadly comprises a system for managing an infusion therapy, including: at least one server in communication with a central server; and a plurality of infusion pumps in wireless communication with the at least one server. Each pump in the plurality of infusion pumps is for: uploading respective label data from a respective label for a respective medication, the respective label data including respective pump programming data for infusion of the respective medication by said each pump; and, wirelessly transmitting respective pump data identifying said each pump to the at least one server. The at least one server is for: transmitting the respective pump data to the central server; receiving, from the central server and in response to receipt of the respective pump data by the central server, respective server pump programming data regarding a respective prescribed medication; and for said each pump, comparing the respective pump programming data with the respective server pump programming data.

The invention further broadly comprises a system for managing an infusion therapy, including: a server in communication with a central server and for downloading, from the central server, a list of patients including respective list pump programming data for patients in the list; and an infusion pump in wireless communication with the server and for uploading respective label data from respective labels for at least one medication, the respective label data including respective label pump programming data for infusion of the at least one medication by the pump. The at least one medication consists of a single medication and the respective label pump programming data consists of first pump programming data. The server is for selecting, from the respective list pump programming data, second pump programming data regarding a second medication; or, when the at least one medication includes a plurality of medications and the respective label pump programming data includes first pump programming data for a first medication from the plurality of medications, the server is for selecting, from the central server and using the pump data and the respective label data, second pump programming data regarding a second medication. The server is for comparing the first pump programming data with the second pump programming data.

The invention broadly comprises a method for managing an infusion therapy.

It is a general object of the present invention to provide a system and method for managing infusion therapies that ensures proper application of infusion therapies while minimizing latency delays and equipment cost and complexity.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE PREFERRED EMBODIMENT

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

It should be understood that the use of "or" in the present application is with respect to a "non-exclusive" arrangement, unless stated otherwise. For example, when saying that "item x is A or B," it is understood that this can mean one of the following: 1) item x is only one or the other of A and B; and 2) item x is both A and B. Alternately stated, the word "or" is not used to define an "exclusive or" arrangement. For example, an "exclusive or" arrangement for the statement "item x is A or B" would require that x can be only one of A and B.

Figure 1:
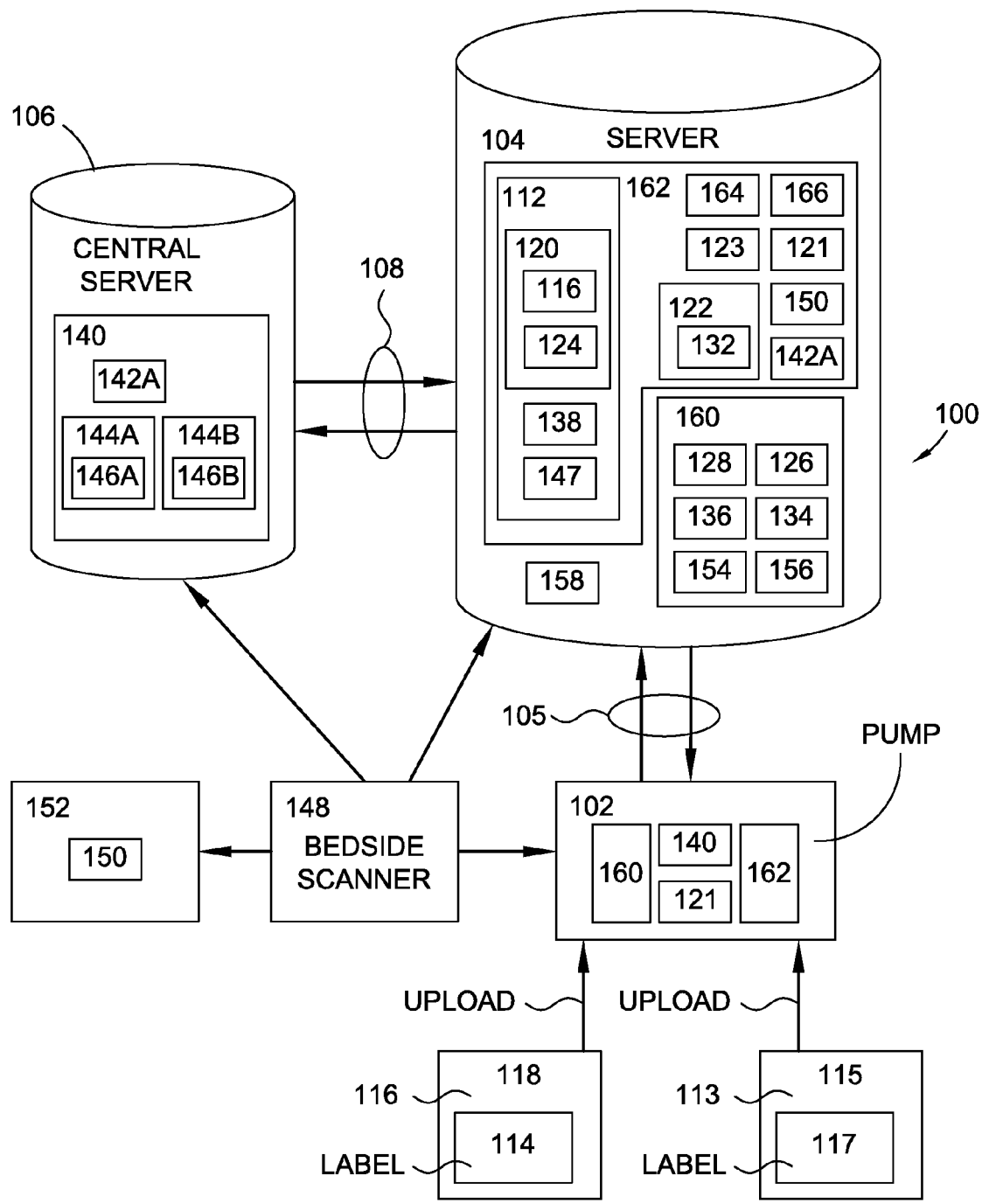
FIG. 1 is a schematic block diagram of a present invention system for managing an infusion therapy.

FIG. 1 is a schematic block diagram of present invention system 100. System 100 includes infusion pump 102 in wireless communication with server 104. The wireless communication can be by any means known in the art, for example, radio frequency link 105. Pump 102 can be any infusion pump known in the art having wireless communications capabilities and programming capabilities sufficient for the operation of pump 102 as described infra. Server 104 can be any server known in the art having wireless communications capabilities and programming capabilities sufficient for the operation of server 104 as described infra.

Server 104 is connected to central server 106 by any means known in the art, including, but not limited to, a hardwire connection, an optical connection, an Internet connection, or a radio frequency connection. Central server 106 can be any server or plurality of servers known in the art. In one embodiment, pump 102, server 104, and server 106 are located in a medical care facility (not shown), for example, a hospital or clinic. In one embodiment (not shown), pump 102 and server 104 are located in one medical care facility, for example, a hospital or clinic and server 106 is in a different/remote location. Server 106 performs centralized data storage and manipulation operations, for example, for a hospital or clinic, as is well known in the art. Server 106 could perform centralized data storage and manipulation for all medical operations in a facility or could be limited to specific portions of the medical operations in a facility. For example, server 106 could be limited to pharmacy operations for the facility. Data described infra with respect to the central server can be entered into the central server and stored or configured within the central server by any means known in the art.

In one embodiment (not shown), more than one server 104 is located in a building or facility and linked with server 106. For example, depending on the size and configuration of the building or facility, the receiving power of server 104, and the transmitting power of pump 102, more than one server 104 may be required for a building or facility.

In one embodiment, the pump is for uploading, that is to say, the pump uploads, respective label data from respective labels for at least one medication. The respective label data including respective label pump programming data for infusion of the at least one medication by the pump. For example, in one embodiment, label data 112 from label 114 for medication 116 in medication dispensing container 118. That is, the at least one medication consists of a single medication. The description that follows is directed to the case of a single medication to be infused using the pump. Other example, embodiments directed to more than one medication to be infused by a pump are described infra. The label data includes label pump programming data 120 for infusion of medication 116 by the pump. Parameters included in label pump programming data described herein, and other pump programming data described infra, can include, but are not limited to: medication identification, medication dosing, time to start infusion, volume to be infused, and patient weight. Data 120 also can include prescription information for medication 116. The pump wirelessly transmits the uploaded label data and pump data 121, identifying the pump, to server 104. Server 104 is for transmitting the pump data to the central server and receiving, from the central server and in response to receipt of the pump data by the central server, server pump programming data 122 for infusion of a medication, presumably, but subject to verification as described infra, medication 116. The central server selects data 122 by a linkage of the pump data in the central server as described infra. For example, a specific set of data, including data 122 is associated with pump 102, via pump data 121, in the central server. The server then compares data 120 and 122.

The preceding paragraph describes a process for confirming that the pumping program on label 114 is accurate and up-to-date. For example, it is possible that one or more of the parameters noted supra for medication 116 have been revised since label 114 was created. In this instance, data 122 includes the revised parameters and server 104 is able to determine that pump programming data including revised parameters is available. As another example, an error may have occurred during the generation of label 114, resulting in an error in program 120. In this instance, server 104 detects the error by comparing data 120 and 122.

In one embodiment, when server 104 determines that data 120 and 122 are the same, server 104 generates and wirelessly transmits, to the pump, authorization signal 126. In one embodiment, the pump displays a message regarding the match of data 120 and 122 in response to receiving the authorization signal. The message provides verification for a caregiver (not shown) operating the pump. In one embodiment, the pump infuses medication 116 only if the authorization signal is received in the pump. This arrangement automatically prevents operation of the pump is there is a problem with program data 120, preventing possible harm to a patient (not shown) receiving an infusion of medication 116.

In one embodiment, when server 104 determines that data 120 and 122 are different, server 104 generates and wirelessly transmits, to the pump, difference signal 128. In one embodiment, the pump displays a message regarding the difference between data 120 and 122 in response to receiving the difference signal. The message provides a warning to a caregiver operating the pump. In one embodiment, the pumping capability of the pump is disabled upon receipt of the difference signal. That is, the pump cannot automatically operate if the difference signal is received. This arrangement automatically prevents operation of the pump is there is a problem with program data 120, preventing possible harm to a patient receiving an infusion of medication 116. In one embodiment, a caregiver is able to manually override the disablement of the pumping capability.

In one embodiment, when server 104 determines that data 120 and 122 are different, and that data 122 is a correct update of data 120, server 104 wirelessly transmits data 122 to the pump. The pump generates and displays message 123 informing a caregiver that correct updated programming data (data 122) has been downloaded into the pump and provides a prompt to begin infusion based on data 122. This arrangement enables a caregiver to quickly start an infusion based on the updated programming data.

In one embodiment, data 112 includes medication data 124 identifying medication 116 and data 122 includes medication identification data 132. Data 132 identifies a medication to be infused using data 122 and that is presumably the same as medication 116, but subject to confirmation as described infra. The server compares data 124 and 132. In one embodiment, when data 124 and 132 match (the respective medications identified in data 124 and 132 are the same), server 104 generates and wirelessly transmits to the pump, authorization signal 134. In one embodiment, the pump displays a message regarding the match of the respective medications in response to receiving authorization signal 134. The message provides verification for a caregiver (not shown) operating the pump. In one embodiment, the pump infuses medication 116 only if authorization signal 134 is received in the pump. This arrangement automatically prevents operation of the pump if there is a problem with medication 116, preventing possible harm to a patient (not shown) scheduled to receive an infusion of medication 116.

In one embodiment, when server 104 determines that the respective medications identified in data 124 and 132 are different, server 104 generates and wirelessly transmits, to the pump, difference signal 136. In one embodiment, the pump displays a message regarding the difference between the medications in response to receiving difference signal 136. The message provides a warning to a caregiver operating the pump. In one embodiment, the pumping capability of the pump is disabled upon receipt of difference signal 136. That is, the pump cannot automatically operate if difference signal 136 is received. This arrangement automatically prevents operation of the pump if there is a problem with medication 116, preventing possible harm to a patient (not shown) scheduled to receive an infusion of medication 116. In one embodiment, a caregiver is able to manually override the disablement of the pumping capability.

In one embodiment, data 112 includes label patient identity 138 identifying a patient for whom medication 116 has been prescribed. The central server stores list 140 of patients including respective list patient identification data 142 and respective list pump programming data 144 for patients in the list. The respective list pump programming data includes respective list medication data 146 identifying a medication or medications to be infused using the respective pump programming data. The central server is arranged to receive, from bedside scanning device 148, pump data 121 and patient data 150 identifying a patient in whom pump 102 is intended to infuse medication 116. Data 121 can be made available for device 148 by any means known in the art, for example, by a barcode (not shown) on the pump. Device 148 can be any device known in the art, and data 150 can be implemented by any means known in the art, for example, barcode 152 on a bracelet (not shown) for the patient mentioned above.

The central server also is arranged to identify, using patient data 150, list patient identification data 142A from data 142 and list pump programming data 144A from data 144. The central server matches patient data 150 with list patient identification data 142A, that is, the identification of the patient for data 150 and 142A are the same. The central server also: correlates patient identification data 142A and pump programming data 144A with pump data 121, for example, flags the data as being related to pump data 121; selects pump programming data 144A as pump programming data 122, using the correlation of patient identification data 142A and pump programming data 144A with pump data 121; and selects, patient identification data 142A using the correlation with the pump data. For example, the central server selects the pump programming data and patient identification data that have been flagged with the pump data. The server receives, from the central server, patient identification data 142A and compares data 138 with patient identification data 142A. In other words, the server determines if the patient to be infused by the pump is the same patient for whom medication 116 has been prescribed according to the label data. Thus, system 100 provides a means for linking, through the pump data, the identification of a patient intended to be infused with a medication with the identification of a patient for whom the medication has been prescribed. In one embodiment (not shown), the scanner is part of pump 102.

In one embodiment, when data 138 and 142A are the same (identify the same patient); server 104 generates and wirelessly transmits to the pump, authorization signal 154. In one embodiment, the pump displays a message regarding the match of data 138 and 142A in response to receiving authorization signal 154. The message provides verification for a caregiver (not shown) operating the pump. In one embodiment, the pump infuses medication 116 only if authorization signal 154 is received in the pump. This arrangement automatically prevents operation of the pump if there is a problem with matching medication 116 to the proper patient, preventing possible harm to a patient (not shown) who might otherwise be incorrectly infused with medication 116.

In one embodiment, when data 138 and 142A are different, server 104 generates and wirelessly transmits to the pump difference signal 156. That is, the patient intended to be infused with a medication is not the patient for whom the medication has been prescribed. In one embodiment, the pump displays a message regarding the difference between data 138 and 142A in response to receiving difference signal 156. The message provides a warning to a caregiver (not shown) operating the pump. In one embodiment, the pumping capability of the pump is disabled upon receipt of difference signal 156. That is, the pump cannot automatically operate if difference signal 156 is received. This arrangement automatically prevents operation of the pump if there is a problem with matching medication 116 to the proper patient, preventing possible harm to a patient (not shown) who might otherwise be incorrectly infused with medication 116. In one embodiment, a caregiver is able to manually override the disablement of the pumping capability.

In one embodiment, pump 102 is adapted for infusing a plurality of medications. In another embodiment, the medications are to be infused sequentially, that is, not concurrently. For example, the pump is adapted to infuse medication 116 in container 118 before medication 113 in container 115. The determination of which medication is to be infused is based on any criterion known in the art, for example, information on labels 114 and 117. It should be understood that the pump can be arranged to sequentially infuse any number of medications, not just the two medications shown in FIG. 1. The pump uploads label data for the first medication to be infused, for example, label data 112 from label 114 for medication 116 in medication dispensing container 118. The label data includes label pump programming data 120 for infusion of medication 116 by the pump. The pump wirelessly transmits the uploaded label data and pump data 121, identifying the pump, to server 104. Server 104 is for transmitting the pump data to the central server and receiving, from the central server and in response to receipt of the pump data by the central server, server pump programming data 122 for infusion of a medication, presumably, but subject to verification as described infra, medication 116. The central server selects data 122 by a linkage of the pump data in the central server as described infra. For example, a specific set of data, including data 122 is associated with pump 102, via pump data 121, in the central server. The server then compares data 120 and 122.

The discussion supra regarding authorization signal 126, difference signal 128, the updating of data 120, and message 123 is applicable to the embodiment under discussion.

In one embodiment, data 112 includes medication data 124 identifying medication 116 and data 122 includes medication identification data 132. Data 132 identifies a medication to be infused using data 122 and that is presumably the same as medication 116, but subject to confirmation as described infra. The server compares data 124 and 132. The discussion supra regarding authorization signal 134 and difference signal 136 is applicable to the embodiment under discussion.

As noted supra, the central server stores list 140 of patients including respective list patient identification data 142 and respective list pump programming data 144 for patients in the list. The respective list pump programming data includes respective list medication data 146 identifying a medication or medications to be infused using the respective pump programming data. As described supra, when the pump is associated with only a single medication to be infused, the pump data uploaded by the pump is sufficient input from the pump for the process of correlating list 140 with the pump. However, when pump 102 is associated with two or more medications to be infused, for example, medications 116 and 113, an additional parameter is needed for the process of correlating list 140 with the pump. In one embodiment, data 112 includes label patient identity 138 identifying a patient for whom medication 116 has been prescribed and label medication identification data 147 identifying medication 116. For example, list 140 includes data 142A for the single patient, pump programming data 144A and 144B, for medications 116 and 113, respectively, and medication identification data 146A and 146B, for medications 116 and 113, respectively.

The central server is arranged to receive, from bedside scanning device 148, the pump data and patient data 150 identifying a patient in whom pump 102 is intended to infuse medication 116. The central server also is arranged to identify, using patient data 150 list patient identification data 142A from data 142. The server matches patient data 150 with list patient identification data 142A, that is, the identification of the patient for data 138 and 142A are the same. However, in the example, in which the pump is associated with medications 116 and 113, there are two list pump programming data and two list medication identification data for the patient. Therefore, in one embodiment, the central server is arranged to identify, using data 147, list medication identification data 146A and list pump programming data 144A from data 144. The server matches data 147 with list medication identification data 146A, that is, data 147 and 146A are the same.

The central server also: correlates patient identification data 142A and pump programming data 144A with the pump data, for example, flags the data as being related to the pump data; selects pump programming data 144A as pump programming data 122, using the correlation of patient identification data 142A and pump programming data 144A with the pump data; and selects, patient identification data 142A using the correlation with the pump data. For example, the central server selects the pump programming data and patient identification data that have been flagged with the pump data. The server receives, from the central server, patient identification data 142A and compares data 138 with patient identification data 142A. In other words, the server determines if the patient to be infused by the pump is the same patient for whom medication 116 has been prescribed according to the label data.

The discussion supra regarding authorization signal 154 and pump difference signal 156 is applicable to the embodiment under discussion.

In one embodiment, pump 102 is adapted for infusing a plurality of medications concurrently. For example, the pump is adapted to infuse medications 116 and 113 concurrently. For example, the pump is a multi-channel pump, for example, with channels 160 and 162 for medications 116 and 113, respectively. It should be understood that the number of medications concurrently infusible, for example, the number of channels in the pump, according to the present invention is not limited to the number shown in FIG. 1 and that other numbers of concurrently infusible medications/channels are included in the spirit and scope of the claimed invention. The discussion supra of pump 102 is applicable to a multi-channel pump, with the exception that instead of uploading pump identification data, for example, pump data 121, identifying the pump, respective channel identification data identifying each channel in the pump is uploaded. For example, channel identification data 164 and 166, identifying channels 160 and 162, respectively, is uploaded. Thus, the channel identification data, for example, channel identification data 164 and 166, is uploaded into the wireless server via the pump, and is uploaded to the central server via the bedside scanner. The operations described supra using pump identification data 121 in the wireless server and in the central server are then performed using the channel identification data, for example, channel identification data 164 or 166. For example, the verification of medications, pump programs, and patient identifications are carried out using the channel identification data, for example, channel identification data 164 or 166. Alternately stated, each channel of the pump is treated as a single pump with a single medication.

In one embodiment, the functions described supra for the central server are performed by server 104. For example, server 104 downloads list 140 from the central server and the bedside scanner transmits data 121 and 150 to server 104, rather than to the central server. For example, server 104: identifies patient identification data 142A, pump programming data 144A, and medication identification data 146A from list 140; correlates patient identification data 142A, pump programming data 144A, and medication identification data 146A with the pump data; selects pump programming data 144A as pump programming data 122, and compares label patient identity 138 with patient identification data 142A.

Figure 2:
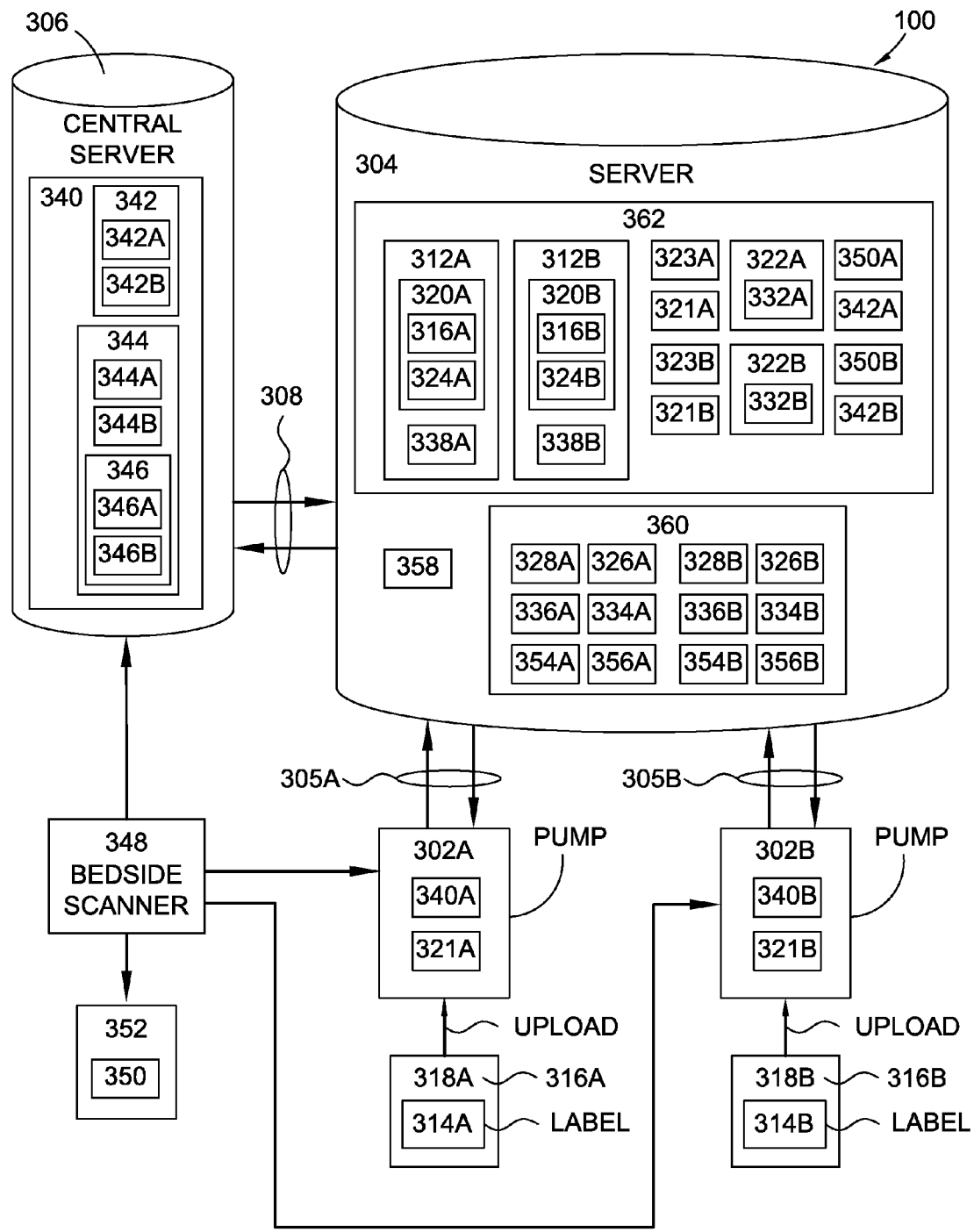
FIG. 2 is a schematic block diagram of a present invention system for managing an infusion therapy; and, FIG. 3 is a flow chart of a present invention method for managing an infusion therapy.
Figure 3:
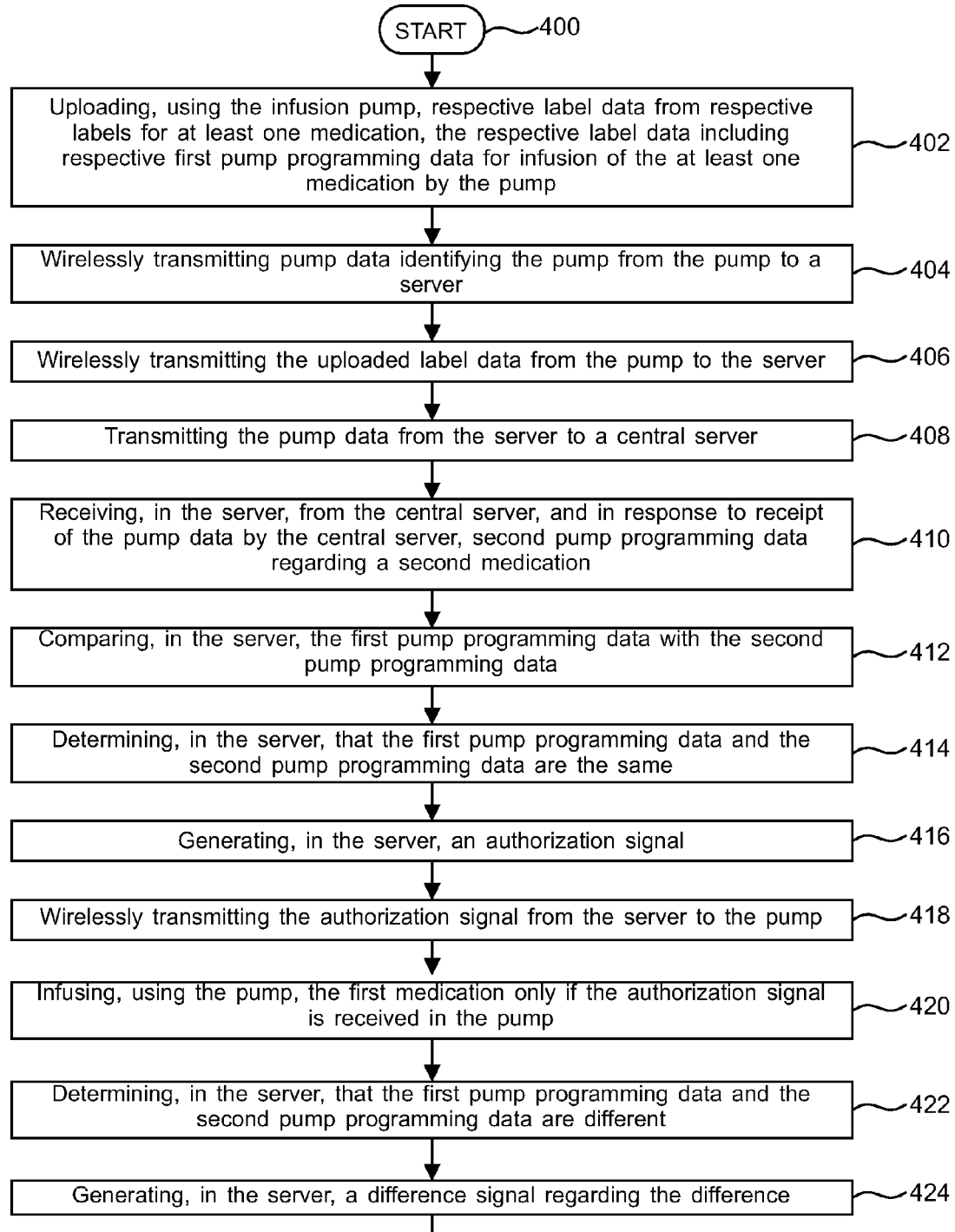
Figure 3:
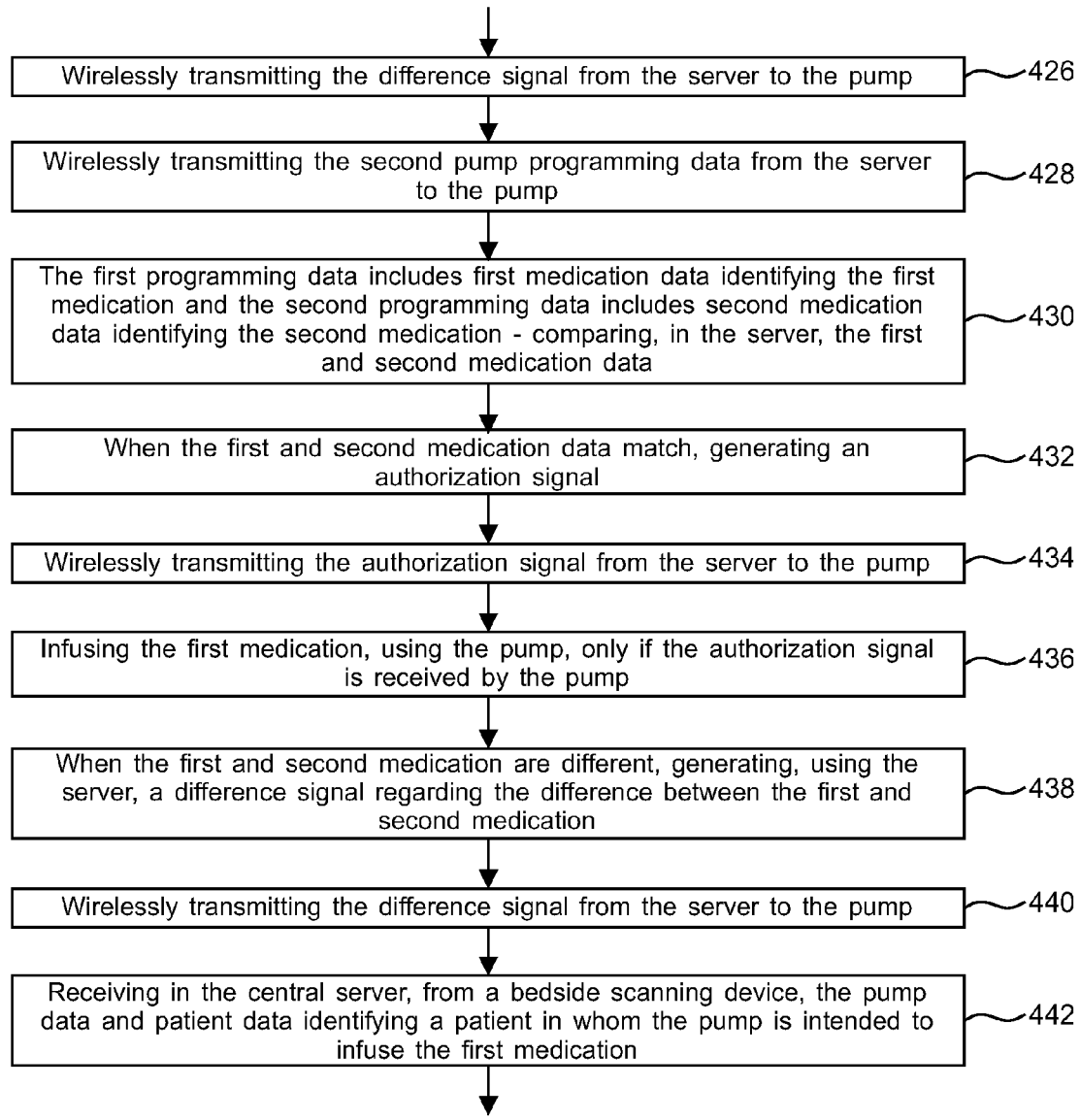
Figure 3:
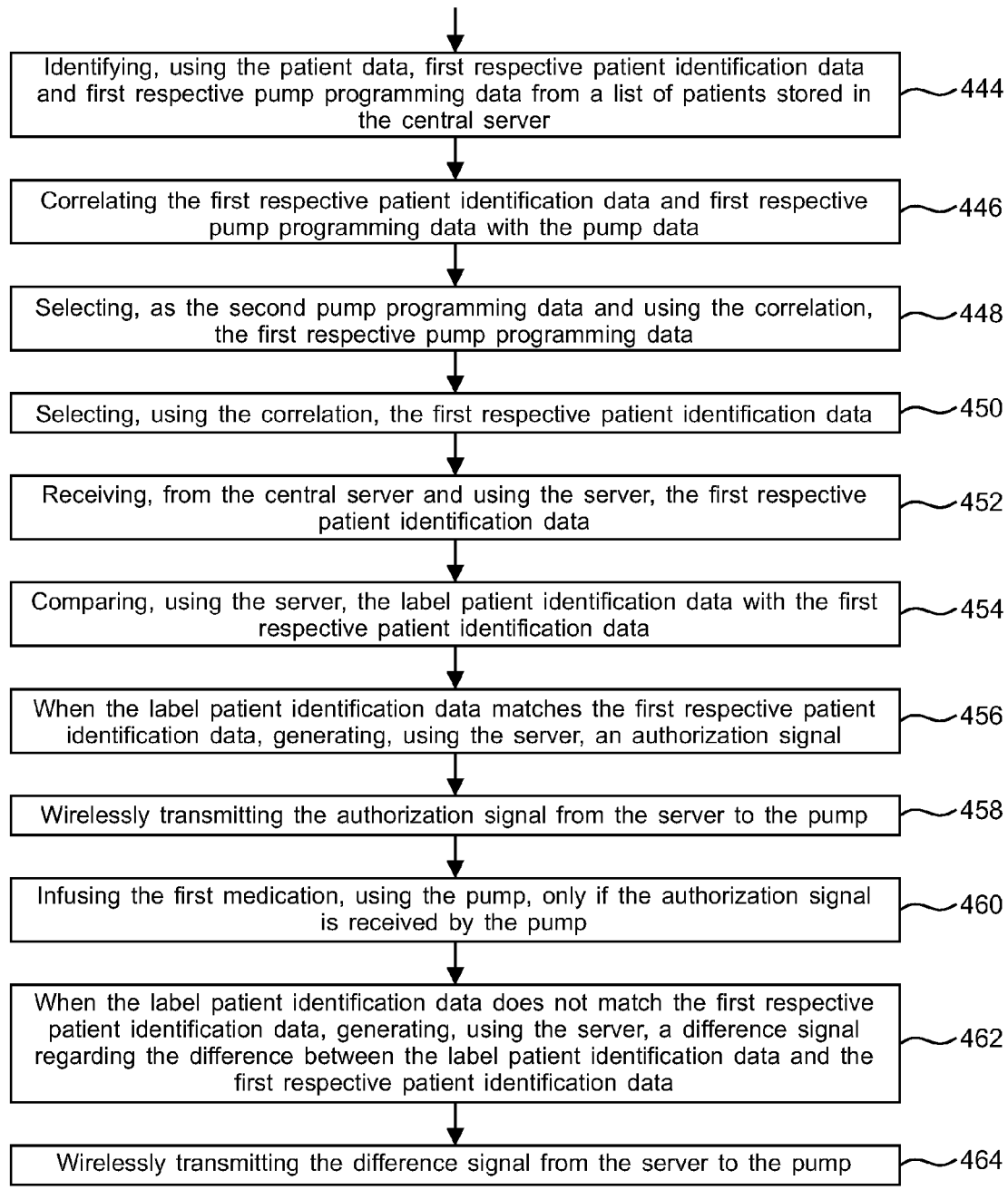

FIG. 2 is a schematic block diagram of present invention system 100. In FIG. 3, system 100 includes a plurality of infusion pumps, for example, pumps 302A and 302B in wireless communication with at least one server, for example, server 304. It should be understood that system 100 is not limited to a particular number of pumps and that other numbers of pumps are included in the spirit and scope of the claimed invention. In particular, FIG. 3 depicts a situation in which a single patient is being infused or will be infused using more than one pumps, for example, two separate pumps such as pumps 302A and 302B. The wireless communication can be by any means known in the art, for example, radio frequency links 305 and 307. Pumps 302A and 302B can be any infusion pumps known in the art having wireless communications capabilities and programming capabilities sufficient for the operation of pumps 302A and 302B as described supra and infra. In general, the description of pump 102 in the discussion of FIG. 1 is applicable to pumps 302A and 302B in FIG. 3. In general, the description of servers 104 and 106 in the discussion of FIG. 1A is applicable to servers 304 and 306 in FIG. 3.

In one embodiment, pumps 302A and 302B upload, respective label data, for example, label data 312A and 312B, from respective labels, for example, labels 314A and 314B, for respective medications, for example, medications 316A and 316B, in respective medication dispensing containers, for example, containers 318A and 318B. The respective label data includes respective pump programming data, for example, data 320A and 320B, for infusion of medications 316A and 316B by pumps 302A and 302B, respectively. Parameters included in the respective pump programming data described herein can include, but are not limited to: medication identification, medication dosing, time to start infusion, volume to be infused, and patient weight. Data 320A and 320B also can include prescription information for medications 316A and 316B. The pumps wirelessly transmits the uploaded label data and respective pump data, for example, pump data 321A and 321B, identifying the respective pump, to server 304. Server 304 is for transmitting the respective pump data to the central server and receiving, from the central server and in response to receipt of the pump data by the central server, respective pump programming data, for example, data 322A and 322B, for infusion of a respective medication, presumably, but subject to verification as described infra, medications 316A and 316B. The central server selects data 322A and 322B by a linkage, correlation, or association of the respective pump data in the central server as described infra. For example, a specific set of data, including data 322A is associated with pump 302A, via pump data 321A, in the central server. The server then compares data 320A and 322A and 320B and 322B.

The preceding paragraph describes a process for confirming that the pumping program on respective labels is accurate and up-to-date. For example, it is possible that one or more of the parameters noted supra for medications 316A or 316B have been revised since the respective label was created. In this instance, data 322A and 322B include the revised parameters and server 304 is able to determine that pump programming data including revised parameters is available. As another example, an error may have occurred during the generation of a respective label, resulting in an error in data 320A or 320B. In this instance, server 304 detects the error by comparing data 320A and 322A and data 320B and 322B.

In one embodiment, when server 304 determines that data 320A and 322A or data 320B and 322B are the same, server 304 generates and wirelessly transmits, to pumps 302A and 302B, respectively, authorization signals 326A and 326B. In one embodiment, pumps 302A and 302B display respective messages regarding the match of data 320A and 322A and data 320B and 322B in response to receiving the respective authorization signal. The message provides verification for a caregiver (not shown) operating the respective pump. In one embodiment, the respective pump infuses the respective medication only if the respective authorization signal is received in the respective pump. This arrangement automatically prevents operation of the respective pump is there is a problem with data 320A or 320B, preventing possible harm to a patient (not shown) receiving an infusion of medication 316A or 316B.

In one embodiment, when server 304 determines that data 320A and 322A or data 320B and 322B are different, server 304 generates and wirelessly transmits, to pump 302A and 302B, difference signal 328A and 328B. respectively. In one embodiment, the respective pump displays a respective message regarding the difference between data 320A and 322A or data 320B and 322B in response to receiving the respective difference signal. The message provides a warning to a caregiver operating the respective pump. In one embodiment, the pumping capability of the respective pump is disabled upon receipt of the respective difference signal. That is, the respective pump cannot automatically operate if the respective difference signal is received. This arrangement automatically prevents operation of the respective pump is there is a problem with data 320A or 320B, preventing possible harm to a patient (not shown) receiving an infusion of medication 316A or 316B. In one embodiment, a caregiver is able to manually override the disablement of the respective pumping capability.

In one embodiment, when server 304 determines that data 320A and 322A or data 320B and 322B are different, and that data 322A or 322B is a correct update of data 320A or 320B, respectively, server 304 wirelessly transmits data 322A or 322B to the respective pump. The respective pump generates and displays a message, for example, message 323A and 323B for pumps 302A and 302B, respectively, informing a caregiver that correct updated programming data (data 322A or 322B) has been downloaded into the respective pump and provides a prompt to begin infusion based on data 322A or 322B. This arrangement enables a caregiver to quickly start an infusion based on the updated programming data.

In one embodiment, label data 312A and 312B include respective label medication data, for example, label medication data 324A and 324B, identifying respective medications, for example, medications 316A and 316B, and data 322A and 322B includes respective medication identification data, for example, medication identification data 332A and 332B. Medication identification data 332A and 332B identifies a respective medication to be infused using data 322A and 322B, respectively, and that is presumably the same as medication medications 316A and 316B, but subject to confirmation as described infra. The server compares data 324A with data 332A and data 324B with data 332B. In one embodiment, when data 324A and data 332A or data 324B and data 332B match (the respective medications identified in label medication data 324A or 324B and medication identification data 332A or 332B are the same), server 304 generates and wirelessly transmits to the pump, respective authorization signals, for example, signals 334A and 334B, respectively. In one embodiment, the respective pump displays a respective message regarding the match of the respective medications in response to receiving a respective authorization signal. The respective message provides verification for a caregiver (not shown) operating the respective pump. In one embodiment, the respective pump infuses medication 316A or 316B only if the respective authorization signal is received in the respective pump. This arrangement automatically prevents operation of the respective pump if there is a problem with medication 316A or 316B, preventing possible harm to a patient (not shown) scheduled to receive an infusion of medication 316A or 316B.

In one embodiment, when server 304 determines that the respective medications identified in data 324A and data 332A or data 324B and data 332B are different, server 304 generates and wirelessly transmits, to the respective pump, a respective difference signal, for example, signals 336A and 336B, respectively. In one embodiment, the respective pump displays a respective message regarding the difference between the respective medications in response to receiving the respective difference signal. The respective message provides a warning to a caregiver operating the respective pump. In one embodiment, the pumping capability of the respective pump is disabled upon receipt of the respective difference signal. That is, the respective pump cannot automatically operate if the difference signal is received. This arrangement automatically prevents operation of the respective pump if there is a problem with medication 316A or 316B, preventing possible harm to a patient (not shown) scheduled to receive an infusion of medication 316A or 316B. In one embodiment, a caregiver is able to manually override the disablement of the pumping capability.

In one embodiment, label data 312A and 312B include respective label patient identity data, for example, label patient identity data 338A and 338B, respectively, identifying a patient for whom medication 316A or 316B, respectively, has been prescribed. The central server stores list 340 of patients including list patient identification data 342 and list pump programming data 344 for patients in the list. The list pump programming data includes list medication data 346 identifying medications to be infused using the list pump programming data.

The central server is arranged to receive, from at least one bedside scanning device, for example, device 348, pump data 321A and 321B and patient data, for example, patient data 350, identifying the patient in whom the respective pump is intended to infuse medication, for example, medications 316A or 316B. Pump data 321A and 321B can be made available for device 348 by any means known in the art, for example, by a respective barcode (not shown) on the respective pump. Device 348 can be any device known in the art, and data 350 can be implemented by any means known in the art, for example, barcode 352 on a bracelet (not shown) for the patient mentioned above. In one embodiment (not shown), the at least one scanner is part of the pumps.

The central server also is arranged to match patient data 350 with respective list patient identification data from list patient identification data 342, for example, match patient data 350 with list patient identity data 342A and 342B. The central server is arranged to match respective label medication identification data with respective list medication data from list medication data 346, for example, match label medication data 324A and 324B with list medication data 346A and 346B. That is, patient data 350 and list patient identity data 342A and 342B are the same and label medication data 324A and 324B and list medication data 346A and 346B, respectively, are the same. Since there is more than one pump for a single patient, using the patient identification alone, as described for FIG. 1, is not sufficient to differentiate between entries in list 340 for the patient. Therefore, an additional parameter, for example, the respective medication identifications, is used to enable the differentiation. It should be understood that other parameters, such as pump programming data, could be used instead of or in addition to the medication identification.

The central server also correlates, or associates, using the matches of the respective list patient identification data and the respective list medication data, respective list pump programming data from list pump programming data 344, respective list patient identification data 342, and respective list medication identification 346, with the respective pump data. For example, using the matches of list patient identity data 342A and 342B and patient data 350 and the matches of list medication identity data 346A and 346B with label medication data 324A and 324B, the central server correlates list pump programming data 344A and 344B with pump data 321A and 321B, respectively. For example, the central server flags list patient identity data 342A and 342B, list pump programming data 344A and 344B, and list medication identity data 346A and 346B with pump data 321A and 321B, respectively. In one embodiment, the central server selects, as the respective second pump programming data and using the respective correlations noted supra, the respective list pump programming data. For example, the central server selects list pump programming data 344A and 344B as pump programming data 322A and 322B, respectively.

In one embodiment, the central server selects the respective patient identification data, for example, data 342A and 342B, using the respective correlations noted supra. For example, in response to receiving data 321A and 321B from server 304, the central server selects data 342A and 342B that have been flagged with respective pump data as noted supra. The at least one server receives from the central server the respective list patient identification data and compares the respective list patient identification data with the respective label patient label identification data, for example, the at least one server compares list patient identity data 342A and 342B with label patient identity data 338A and 338B, respectively. In other words, the at least one server determines if the patient to be infused by the respective pump is the same patient for whom medication 316A or 316B has been prescribed according to the respective label data. Thus, system 100 provides a means for linking, through the respective pump data, the identification of a patient intended to be infused with a medication with the identification of a patient for whom the medication has been prescribed.

In one embodiment, when the respective list patient identification data matches the respective label patient identification data, for example, list patient identity data 342A or 342B and label patient identity data 338A or 338B, respectively, are the same (identify the same patient); server 304 generates and wirelessly transmits to the respective pump, a respective authorization signal, for example, signals 354A and 354B. In one embodiment, when the respective list patient identification data does not match the respective label patient identification data, for example, list patient identity data 342A or 342B and label patient identity data 338A or 338B, respectively, are not the same (do not identify the same patient); server 304 generates and wirelessly transmits to the respective pump, a respective difference signal, for example, signals 356A and 356B.

The discussion in the description of FIG. 1 with respect to messages regarding the data matches, infusing medication only if an authorization signal is received, displaying a message regarding a difference in data, disabling pumping capability of the pump upon receipt of a difference signal, and manually override the disablement of the pumping capability, is applicable to FIG. 3.

The following is a summary of a process involving one embodiment of a present invention system. A bedside scanner, for example, scanner 148, scans identification data for an infusion pump, for example, data 121 for pump 102, and identification data for a patient, for example, data 150, and transmits the data to a central server, for example, server 106. The central server correlates a list of patients, for example, list 140, and respective data, such as data 142 and 144 with data 121. The pump wirelessly transmits the pump identification data, for example, data 121, and information from a medication barcode, for example, data 112 from label 114, to a wireless server, for example, server 104. The barcode includes patient, medication, and prescription/pump programming data, for example, data 138, 116, and 120, respectively. The wireless server transmits the pump identification data to the central server. Using the correlation, the central server selects the respective data associated with the pump data and transmits the respective data to the wireless server. The associated data can include patient identification, drug identification, and pump programming/prescription data. The wireless server compares some or all of the patient identification, drug identification, and pump programming/prescription data from the central server with the label data to ensure that the right patient, right drug, and right prescription are being implemented with the pump.

The present invention also comprises a server, for example, server 104, for managing an infusion therapy. The server includes interface element 158, processor 160, and memory element 162. By interface element, we mean any combination of hardware, firmware, or software in a processor-based device used to enable communication or data transfer between the device and a device, system, or network external to the computer. The interface element can connect with the device, system, or network external to the computer, for example, pump 102 and server 106, using any means known in the art, including, but not limited to a hardwire connection, an optical connection, an Internet connection, or a wireless connection, such as a radio frequency connection. Processor 160 and interface element 158 can be any processor or interface element, respectively, or combination thereof, known in the art. In one embodiment, the various data described supra are stored in the memory element.

FIG. 1 is used in the following discussion; however it should be understood that the discussion also is applicable to FIGS. 2 and 3. The interface element wirelessly uploads, from an infusion pump, for example, pump 102, label data, for example, data 112, from a label, for example, label 114, for a first medication, for example, medication 116. The label data includes pump programming data, for example, data 120, for administering the first medication, medication data, for example, data 124, identifying the first medication and patient data, for example, data 138, identifying a patient for whom the first medication is intended. The label data uploaded from the label by the pump. The interface element also wirelessly uploads, from the infusion pump, pump data, for example, data 121, identifying the pump, transmits the pump data to a central server, for example, server 106, and receives, from the central server, pump programming data, for example, data 122, for administering a second medication, medication data, for example, data 132, identifying the second medication, and patient data, for example, data 144, identifying a patient for whom the second medication is intended.

The processor compares the first patient, medication, and pump programming data with the second patient, medication, and pump programming data, respectively. For a match of the first patient, medication, and pump programming data, with the second patient, medication, or pump programming data, respectively, generating an authorization signal, for example, signal 126, 134, or 146. The interface element is for wirelessly transmitting the authorization signal to the infusion pump. For a mismatch of the first patient, medication, or pump programming data, with the second patient, medication, or pump programming data, respectively, the processor generates a difference signal, for example, signal 128, 136, or 148. The interface element wirelessly transmits to the pump the difference signal regarding the mismatch.

The central server transmits relevant information regarding the patient associated with the pump identification to the wireless server. For example, the central server receives the patient identification from the bedside scanner, selects appropriate and updated information such as medication and prescription/programming data for the patient, and transmits the updated information to the wireless server. The wireless server compares the patient, medication, and prescription/programming data received from the central server with the scanned data from the medication barcode to ensure that the right patient is given the right medication according to the right prescription/pump program. The wireless server sends a confirmation signal to the pump if the patient, medication, and prescription/programming data match. If the patient and medication data match, but the prescription/programming data has been updated or revised, the wireless server wirelessly transmits or sends the updated or revised prescription/programming data to the pump.

Medical institutions are striving to reduce medication errors, especially those associated with the use of an infusion pump. The typical goal of a medication error reduction system is to ensure the five rights of medication delivery: Right patient, Right medication, Right dose, Right time, and Right route. Typical errors that can occur in the process of delivering medication to a patient include:

1. Associating the wrong medication for the patient, that is, giving the wrong medication to the patient;
2. Associating the wrong patient with the medication, that is, giving medication to the wrong patient; and,
3. Delivering the medication according to an outdated prescription or pump program.

A present invention system addresses each of the three problems noted above.

As noted supra, some prior art medication management systems use a bedside point of care device with processing capability, for example, a computer, to acquire and compare patient, medication, and prescription data. Thus, the prior art teaches away from system 100, which places the comparison functionality in a wireless server that can interface with a large number of pumps.

FIG. 3 is a flow chart illustrating a present invention method for managing an infusion therapy. Although the method in FIG. 2 is depicted as a sequence of numbered steps for clarity, no order should be inferred from the numbering unless explicitly stated. The method starts at Step 400. Step 402 uploads, using the infusion pump, respective label data from respective labels for at least one medication, the respective label data including respective first pump programming data for infusion of the at least one medication by the pump; step 404 wirelessly transmits pump data identifying the pump from the pump to a server; step 406 wirelessly transmits the uploaded label data from the pump to the server; step 408 transmits the pump data from the server to the central server; step 410 receives, in the server, from the central server, and in response to receipt of the pump data by the central server, second pump programming data regarding a second medication; and step 412 compares, in the server, the first pump programming data with the second pump programming data.

In one embodiment: step 414 determines, in the server, that the first pump programming data and the second pump programming data are the same; step 416 generates, in the server, an authorization signal; and step 418 wirelessly transmits the authorization signal from the server to the pump. In one embodiment, step 420 infuses, using the pump, the first medication only if the authorization signal is received in the pump.

In another embodiment: step 422 determines, in the server, that the first pump programming data and the second pump programming data are different; step 424 generates, in the server, a difference signal regarding the difference; and step 426 wirelessly transmits the difference signal from the server to the pump. In one embodiment, step 428 wirelessly transmits the second pump programming data from the server to the pump.

In one embodiment, the first programming data includes first medication data identifying the first medication and the second programming data includes second medication data identifying the second medication and step 430 compares, in the server, the first and second medication data; step 432 when the first and second medication data match, generates an authorization signal; step 434 wirelessly transmits the authorization signal to the pump; step 436 infuses the first medication, using the pump, only if the authorization signal is received by the pump; step 438, when the first and second medication data are different, generates, using the server, a difference signal regarding the difference between the first and second medications; and step 440 wirelessly transmits the difference signal from the server to the pump.

In one embodiment, the respective label data includes first medication identification data identifying the first medication and label patient identification data identifying a patient for whom the first medication is prescribed, the central server stores a list of patients including respective patient identification data and respective pump programming data for patients in the list, and the respective pump programming data includes respective medication data identifying medications to be infused using the respective pump programming data. The following steps are implemented in the central server: step 442 receives, from a bedside scanning device, the pump data and patient data identifying a patient in whom the pump is intended to infuse the first medication; step 444 identifies, using the patient data, first respective patient identification data and first respective pump programming data from the list of patients, the identification of the patient for the patient data and for the first respective patient identification data being the same; step 446 correlates the first respective patient identification data and first respective pump programming data with the pump data; step 448 selects, as the second pump programming data and using the correlation, the first respective pump programming data; and step 450 selects, using the correlation, the first respective patient identification data. Step 452 receives, from the central server and using the server, the first respective patient identification data; step 454 compares, using the server, the label patient identification data with the first respective patient identification data; step 456, when the label patient identification data matches the first respective patient identification data, generates, using the server, an authorization signal; step 458 wirelessly transmits the authorization signal from the server to the pump; step 460 infuses the first medication, using the pump, only if the authorization signal is received by the pump; step 462, when the label patient identification data does not match the first respective patient identification data, generates, using the server, a difference signal regarding the difference between the label patient identification data and the first respective patient identification data; and step 464 wirelessly transmits the difference signal from the server to the pump.

The present invention also includes a method for managing an infusion therapy using a plurality of pumps. Although the method is described as a sequence of steps for clarity, no order should be inferred from the sequence unless explicitly stated. A first step uploads to a plurality of infusion pumps, respective label data from a respective label for a respective first medication, the respective label data including respective first pump programming data for infusion of the respective first medication by said each pump; a second step wirelessly transmits from the plurality of infusion pumps to at least one server, respective pump data identifying said each pump to the at least one server; a third step wirelessly transmits the uploaded respective label data from the plurality of infusion pumps to at least one server; a fourth step transmits the respective pump data from the at least one server to a central server; a fifth step receives, in the at least one server, from the central server, and in response to receipt of the respective pump data by the central server, respective second pump programming data regarding a respective second medication; and a sixth step compares, in the at least one server and for said each pump, the respective first pump programming data with the respective second pump programming data.

In one embodiment, when the respective first pump programming data matches the respective second pump programming data, a seventh step generates and wirelessly transmits to the at least one pump, using the at least one server, at least one authorization signal. In one embodiment, when the respective first pump programming data does not match the respective second pump programming data, an eighth step generates and wirelessly transmits to the at least one pump, using the at least one server, at least one difference signal.

In one embodiment, the respective first programming data includes respective first medication data identifying the respective first medication and the respective second pump programming data includes respective second medication data identifying the respective second medication and: a ninth step compares, using the at least one server, the respective first and second medication data; and, when the respective first and second medication data match, a tenth step generates and wirelessly transmits to the at least one pump, using the at least one server, at least one authorization signal; or, when the respective first and second medication data do not match, an eleventh step generates and wirelessly transmits to the at least one pump, using the at least one server, at least one difference signal.

In one embodiment, the respective label data includes respective label patient identification data identifying a patient for whom the respective first medication is prescribed and respective label medication identification data identifying the respective first medication, the central server stores a list of patients including list patient identification data and list pump programming data for patients in the list, the list pump programming data includes list medication data identifying medications to be infused using the list pump programming data, and: a twelfth step receives, in the central server and from at least one bedside scanning device, the respective pump data and respective patient data identifying a respective patient in whom the respective pump is intended to infuse the respective first medication; a thirteenth step matches, in the central server, the respective label patient identification data with respective list patient identification data from the list patient identification data; a fourteenth step matches, in the central server, the respective label medication identification data with respective list medication data from the list medication data; a fifteenth step correlates, in the central server and using the matches of the respective list patient identification data and the respective list medication data, respective list pump programming data from the list pump programming data with the respective pump data; a sixteenth step selects, in the central server and using the respective correlations, the respective list pump programming data as the respective second pump programming data; a seventeenth step selects, in the central server and using the respective correlations, the respective list patient identification data; an eighteenth step receives, in the at least one server and from the central server, the respective list patient identification data; and a nineteenth step compares, in the at least one server, the respective list patient identification data with the respective label patient label identification data.

In one embodiment, when the respective list patient identification data matches the respective label patient identification data, a twentieth step generates and wirelessly transmits to the at least one pump, using the at least one server, at least one authorization signal. In one embodiment, when the respective list patient identification data does not match the respective label patient identification data, a twenty first step generates and wirelessly transmits to the at least one pump, using the at least one server, at least one difference signal.

The present invention further includes a method for managing an infusion therapy. Although the method is described as a sequence of steps for clarity, no order should be inferred from the sequence unless explicitly stated. A first step downloads, from a central server to a server, a list of patients including respective list pump programming data for patients in the list; a second step uploads, to an infusion pump in wireless communication with the server, respective label data from respective labels for at least one medication, the respective label data including respective label pump programming data for infusion of the at least one medication by the pump; and, when the at least one medication consists of a single medication and the respective label pump programming data consists of first pump programming data, a third step selects, in the server and from the respective list pump programming data, second pump programming data regarding a second medication; or, when the at least one medication includes a plurality of medications and the respective label pump programming data includes first pump programming data for a first medication from the plurality of medications, a fourth step selects, in the server and from the central server and using the pump data and the respective label data, second pump programming data regarding a second medication; a fifth step compares, in the server, the first pump programming data with the second pump programming data.

In one embodiment, the respective label data includes label patient data identifying the patient for whom the at least one medication is prescribed, and first medication identification data identifying the first medication, and the list of patients includes respective list patient identification data and respective prescribed medication identification data for patients in the list. A sixth step receives, in the server and from a bedside scanning device, the pump data and patient data identifying a patient in whom the pump is intended to infuse the at least one medication; and a seventh step identifies, in the server, first list patient identification data, first list pump programming data, and first prescribed medication identification data from the list of patients by using the patient data, the identification of the patient for the patient data and for the first list patient identification data being the same; or, and eighth step identifies, in the server, first list patient identification data, first list pump programming data, and first prescribed medication identification data from the list of patients by using the patient data and the first medication identification data. The identification of the patient for the patient data and for the first list patient identification data are the same and the respective medication identified by the first medication identification data and the first list prescribed medication identification data are the same. A ninth step correlates, in the server, the first list patient identification data and the first list pump programming data with the pump data; or, a tenth step correlates, in the server, the first list patient identification data, the first list pump programming data, and the first prescribed medication identification data with the pump data. An eleventh step selects, in the server, the first list pump programming data as the second pump programming data by using the correlation of the first list patient identification data, the first list pump programming data, or the first prescribed medication identification data with the pump data; and, a twelfth step compares, in the server, the label patient identification data with the first list patient identification data.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed is:

1. A system for managing an infusion therapy, comprising:
a server in communication with a central server; and,
an infusion pump in wireless communication with the server and for:
wirelessly transmitting pump data identifying the pump to the server;
uploading respective label data from respective labels for at least one medication, the respective label data including respective label pump programming data for infusion of the at least one medication by the pump; and,
wirelessly transmitting, to the server, the respective label data wherein:
when the at least one medication consists of a single medication and the respective label pump programming data consists of first pump programming data, the server is for:
transmitting the pump data to the central server;
receiving, from the central server and in response to receipt of the pump data by the central server, second pump programming data regarding a second medication; and,
comparing the first pump programming data with the second pump programming data; or,
when the at least one medication includes a plurality of medications and the respective label pump programming data includes first pump programming data for a first medication from the plurality of medications, the server is for:
transmitting the pump data and the respective label data to the central server;
receiving, from the central server and in response to receipt of the pump data and the respective label data by the central server, second pump programming data regarding a second medication; and,
comparing the first pump programming data with the second pump programming data.

2. The system of claim 1 wherein when the first pump programming data is the same as the second pump programming data, the server is for generating and wirelessly transmitting to the pump an authorization signal; or wherein when the first pump programming data is the same as the second pump programming data, the server is for, generating and wirelessly transmitting to the pump an authorization signal and wherein the pump is for infusing the first medication only if the authorization signal is received in the pump.

3. The system of claim 1 wherein when the first pump programming data is the not the same as the second pump programming data, the server is for, generating and wirelessly transmitting to the pump a difference signal regarding the difference between the first and second pump programming data; or wherein when the first pump programming data is the same as the second pump programming data, the server is for, generating and wirelessly transmitting to the pump a difference signal regarding the difference between the first and second pump programming data; and wirelessly transmitting to the pump the second pump programming data.

4. The system of claim 1 wherein the respective label programming data includes first medication data identifying the single medication or the first medication, and the second pump programming data includes second medication data identifying the second medication and wherein the server is for comparing the first and second medication data and when the first and second medication data match, generating and wirelessly transmitting to the pump an authorization signal; or wherein the first programming data includes first medication data identifying the first medication or the at least one medication, and the second pump programming data includes second medication data identifying the second medication; wherein the server is for comparing the first and second medication data and when the first and second medication data match, generating and wirelessly transmitting to the pump an authorization signal, and wherein the pump is for infusing the first medication only if the authorization signal is received by the pump.

5. The system of claim 1 wherein the respective first programming data includes first medication data identifying the single medication or the first medication, and the second pump programming data includes second medication data identifying the second medication, wherein the server is for comparing the first and second medication data and when the first and second medication data are different, generating and wirelessly transmitting to the pump a difference signal regarding the difference between the first and second medications.

6. The system of claim 1 wherein the respective label data includes label patient data identifying the patient for whom the at least one medication is prescribed, and first medication identification data identifying the first medication, wherein the central server stores a list of patients including respective list patient identification data, respective list pump programming data, and respective prescribed medication identification data for patients in the list, and wherein the central server is arranged to:
receive, from a bedside scanning device, the pump data and patient data identifying a patient in whom the pump is intended to infuse the at least one medication; and,
wherein the central server is arranged to:

identify first list patient identification data, first list pump programming data, and first prescribed medication identification data from the list of patients by using the patient data, the identification of the patient for the patient data and for the first list patient identification data being the same; or wherein the server is arranged to:

identify first list patient identification data, first list pump programming data, and first prescribed medication identification data from the list of patients by using the patient data and the first medication identification data, wherein the identification of the patient for the patient data and for the first list patient identification data are the same and the respective medication identified by the first medication identification data and the first list prescribed medication identification data are the same; and, wherein the central server is arranged to:

correlate the first list patient identification data and the first list pump programming data with the pump data; or, correlate the first list patient identification data, the first list pump programming data, and the first prescribed medication identification data with the pump data; and wherein the central server is arranged to:

select the first list pump programming data as the second pump programming data by using the correlation of the first list patient identification data, the first list pump programming data, or the first prescribed medication identification data with the pump data, wherein the server is for receiving, from the central server, the first list patient identification data; and comparing the label patient identification data with the first list patient identification data.

7. The system of claim 6 wherein when the label patient identification data matches the first list patient identification data, the server is for generating and wirelessly transmitting to the pump an authorization signal; or wherein when the label patient identification data matches the first list patient identification data, the server is for generating and wirelessly transmitting to the pump an authorization signal and wherein the pump is for infusing the first medication only if the authorization signal is received by the pump.

8. The system of claim 6 wherein when the label patient identification data does not match the first list patient identification data, the server is for generating and wirelessly transmitting to the pump a difference signal regarding the difference between the label patient identification data and the first list patient identification data.

9. The system of claim 1 further comprising a plurality of the infusion pumps in wireless communication with the server.

10. The system of claim 1 wherein the pump includes a plurality of channels, wherein each channel in the plurality of channels is arranged to infuse a respective third medication, wherein for each channel in the plurality of channels, the pump is for:

wirelessly transmitting channel data identifying the channel to the server;

uploading label data from the respective third medication, the label data including respective third programming data for infusion of the respective third medication by said each channel; and, wirelessly transmitting, to the server, the label data from the respective third medication, wherein the server is for:

transmitting the channel data to the central server; and, receiving, from the central server and in response to receipt of the channel data by the central server, respective fourth pump programming data regarding a respective fourth medication, and wherein the server is for comparing the respective third pump programming data with the respective fourth pump programming data.

11. A system for managing an infusion therapy, comprising:

a server in communication with a central server and for downloading, from the central server, a list of patients including respective list pump programming data for patients in the list; and, an infusion pump in wireless communication with the server and for uploading respective label data from respective labels for at least one medication, the respective label data including respective label pump programming data for infusion of the at least one medication by the pump; and, wherein when the at least one medication consists of a single medication and the respective label pump programming data consists of first pump programming data, the server is for selecting, from the respective list pump programming data, second pump programming data regarding a second medication; or, wherein, when the at least one medication includes a plurality of medications and the respective label pump programming data includes first pump programming data for a first medication from the plurality of medications, the server is for selecting, from the central server and using the pump data and the respective label data, second pump programming data regarding a second medication; and, wherein the server is for comparing the first pump programming data with the second pump programming data.

12. The system of claim 11 wherein the respective label data includes label patient data identifying the patient for whom the at least one medication is prescribed, and first medication identification data identifying the first medication, wherein the list of patients includes respective list patient identification data and respective prescribed medication identification data for patients in the list, and wherein the server is for receiving, from a bedside scanning device, the pump data and patient data identifying a patient in whom the pump is intended to infuse the at least one medication; and, wherein the server is for: identify first list patient identification data, first list pump programming data, and first prescribed medication identification data from the list of patients by using the patient data, the identification of the patient for the patient data and for the first list patient identification data being the same; or, identifying first list patient identification data, first list pump programming data, and first prescribed medication identification data from the list of patients by using the patient data and the first medication identification data, wherein the identification of the patient for the patient data and for the first list patient identification data are the same and the respective medication identified by the first medication identification data and the first list prescribed medication identification data are the same; and, wherein the server is for:

correlating the first list patient identification data and the first list pump programming data with the pump data; or, correlating the first list patient identification data, the first list pump programming data, and the first prescribed medication identification data with the pump data; and, wherein the server is for:

selecting the first list pump programming data as the second pump programming data by using the correlation of the first list patient identification data, the first list pump programming data, or the first prescribed medication identification data with the pump data; and, comparing the label patient identification data with the first list patient identification data.

* * * * *